US009513227B2

(12) United States Patent
Onodera et al.

(10) Patent No.: US 9,513,227 B2
(45) Date of Patent: Dec. 6, 2016

(54) METHOD FOR QUANTITATIVE DETERMINATION OF OXIDANT AND APPARATUS FOR QUANTITATIVE DETERMINATION OF OXIDANT

(71) Applicant: Panasonic Intellectual Property Management Co., Ltd., Osaka (JP)

(72) Inventors: Mari Onodera, Osaka (JP); Shin-ichi Imai, Osaka (JP); Hironori Kumagai, Osaka (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 0 days.

(21) Appl. No.: 14/409,956

(22) PCT Filed: Apr. 21, 2014

(86) PCT No.: PCT/JP2014/002220
§ 371 (c)(1),
(2) Date: Dec. 19, 2014

(87) PCT Pub. No.: WO2014/174818
PCT Pub. Date: Oct. 30, 2014

(65) Prior Publication Data
US 2016/0011118 A1 Jan. 14, 2016

(30) Foreign Application Priority Data
Apr. 26, 2013 (JP) ................................. 2013-094231

(51) Int. Cl.
*G01N 31/00* (2006.01)
*G01N 35/02* (2006.01)
(Continued)

(52) U.S. Cl.
CPC .............. *G01N 21/75* (2013.01); *G01N 21/31* (2013.01); *G01N 21/78* (2013.01); *G01N 31/005* (2013.01);
(Continued)

(58) Field of Classification Search
CPC ...... G01N 21/75; G01N 21/31; G01N 21/25; G01N 21/17; G01N 21/00; G01N 31/005; G01N 31/00; G01N 25/48; G01N 25/4846; G01N 25/20; G01N 25/00; G01N 35/025; G01N 35/02; G01N 35/00; Y10T 436/10; Y10T 436/101666
USPC .......................... 436/10, 8; 422/50, 51, 68.1
See application file for complete search history.

(56) References Cited

U.S. PATENT DOCUMENTS 4,539,296 A 9/1985 Manabe
4,670,385 A 6/1987 Babb et al.
(Continued)

FOREIGN PATENT DOCUMENTS

JP 57-072047 A 5/1982
JP 60-256056 A 12/1985
(Continued)

OTHER PUBLICATIONS

International Search Report issued in PCT/JP2014/002220, dated Jul. 8, 2014, with English translation.
(Continued)

*Primary Examiner* — Christine T Mui
(74) *Attorney, Agent, or Firm* — McDermott Will & Emery LLP

(57) ABSTRACT

The present invention provides a method for quantitative determination of oxidant which method is capable of accurately and rapidly performing quantitative determination of oxidant at low cost, and an apparatus for quantitative determination of oxidant used in the method. The method for quantitative determination of oxidant according to the present invention is a method for quantitative determination of oxidant performing quantitative determination of oxidant in a sample using a redox reaction, the method including: adding one kind of reducing agent to a sample solution containing one or a plurality of kinds of oxidants having different lifetimes; producing an absorbance curve by measuring a time change in absorbance of the post-color-change or post-coloring reducing agent; and performing the quantitative determination of the oxidant while identifying the oxidant in the sample solution based on the obtained absorbance curve.

10 Claims, 7 Drawing Sheets

(51) Int. Cl.
*G01N 21/75* (2006.01)
*G01N 21/78* (2006.01)
*G01N 21/31* (2006.01)
*G01N 31/22* (2006.01)

(52) U.S. Cl.
CPC ....... *G01N 31/228* (2013.01); *G01N 2021/755* (2013.01); *G01N 2201/061* (2013.01); *G01N 2201/127* (2013.01)

(56) References Cited

U.S. PATENT DOCUMENTS

| | | | |
|---|---|---|---|
| 4,855,228 | A | 8/1989 | Charlton et al. |
| 5,420,042 | A | 5/1995 | Schafer et al. |
| 6,156,577 | A | 12/2000 | Miyazawa et al. |
| 2003/0166295 | A1 | 9/2003 | Fukuoka et al. |
| 2003/0175984 | A1 | 9/2003 | Fukuoka et al. |
| 2003/0175985 | A1 | 9/2003 | Fukuoka et al. |
| 2003/0180183 | A1 | 9/2003 | Fukuoka et al. |
| 2003/0203503 | A1 | 10/2003 | Fukuoka et al. |
| 2004/0234992 | A1 | 11/2004 | Cotton et al. |
| 2008/0305553 | A1 | 12/2008 | Kraus |
| 2009/0145202 | A1 | 6/2009 | Tokhtuev et al. |
| 2009/0147822 | A1 | 6/2009 | Tokhtuev et al. |
| 2009/0150086 | A1 | 6/2009 | Tokhtuev et al. |
| 2009/0150106 | A1 | 6/2009 | Erickson et al. |
| 2012/0149121 | A1 | 6/2012 | Tokhtuev et al. |
| 2013/0046480 | A1 | 2/2013 | Manri et al. |
| 2013/0122596 | A1 | 5/2013 | Kamihara et al. |
| 2014/0141523 | A1 | 5/2014 | Tokhtuev et al. |

FOREIGN PATENT DOCUMENTS

| | | |
|---|---|---|
| JP | 61-184463 A | 8/1986 |
| JP | 01-109261 A | 4/1989 |
| JP | 08-080199 A | 3/1996 |
| JP | 09-184836 A | 7/1997 |
| JP | 10-282001 A | 10/1998 |
| JP | 2003-262612 A | 9/2003 |
| JP | 2005-526230 A | 9/2005 |
| JP | 2010-529451 A | 8/2010 |
| JP | 2011-094970 A | 5/2011 |
| WO | 2011-132525 A1 | 10/2011 |
| WO | 2012-008324 A1 | 1/2012 |

OTHER PUBLICATIONS

English Translation of International Preliminary Report on Patentability and Notification of Transmittal issued on Nov. 5, 2015 in International Application No. PCT/JP2014/002220.

METHOD FOR QUANTITATIVE DETERMINATION OF OXIDANT AND APPARATUS FOR QUANTITATIVE DETERMINATION OF OXIDANT

RELATED APPLICATIONS

This application is the U.S. National Phase under 35 U.S.C. §371 of International Application No. PCT/JP2014/002220, filed on Apr. 21, 2014, which in turn claims the benefit of Japanese Application No. 2013-094231, filed on Apr. 26, 2013, the disclosures of which Applications are incorporated by reference herein.

TECHNICAL FIELD

The present invention relates to a method for quantitative determination of oxidant using a redox reaction, and an apparatus for quantitative determination of oxidant used in the method.

BACKGROUND ART

In many fields, it is important to detect or quantify an oxidant and a substance that generates an oxidant as a result of a chemical reaction. Particularly, in the water treatment field, it is very important to quantify and monitor an oxidant in water in order to manage a water treatment effect and operation of a water treatment apparatus.

Conventionally, for example, an enzymatic method or a method for measuring a substance that chemically reacts with an analyte to generate a detectable change (such as a color change) is proposed as a method for quantitative determination of oxidant, and used in quantitative determination of various components existing in a body fluid in a clinical inspection or an environmental analysis. For example, in the quantitative determination of hydrogen peroxide, under coexistence of peroxidase, a substance such as leuco dye in which the detectable color change is generated is added as a reducing agent to cause a redox reaction, and a quantitatively-produced coloring substance is subjected to a colorimetric analysis (for example, see Patent Document 1).

PRIOR ART DOCUMENT

Patent Document

Patent Document: Unexamined Japanese Patent Publication No. S60-256056

DISCLOSURE OF INVENTION

Problems to be Solved by Invention

However, in the conventional method, an error is easily generated due to blank coloring caused by the natural oxidation of a reducing agent that is used as a reagent, which results in a problem in that accurate quantitative determination is hardly performed. In contrast, there is a method for adding a masking agent to prevent the natural oxidation of a reducing agent. However, because an effect of the masking agent is affected by sample water quality such as pH or metal ions, the method cannot be applied to all kinds of sample water. There is also a method for correcting the blank coloring by a blank test. However, it takes a long time to prepare and perform the blank test. Therefore, there is a need for the method for quantitative determination of oxidant which method is capable of accurately performing quantitative determination of oxidant with no use of masking agent or blank test.

For a well-known oxidant contained in sample water, a reducing agent having high selectivity to the well-known oxidant is selected and used. However, for an unknown oxidant contained in sample water, it is necessary to use a general reducing agent. In such cases, the redox reaction may not quantitatively progress, and the accurate quantitative determination may be hardly performed. When the accurate quantitative determination can be performed even if one kind of reducing agent is used with respect to various oxidants, it is not necessary to prepare various reducing agents, which allows the quantitative determination to be rapidly performed at low cost.

The present invention has been made to solve the above problems, and an object of the present invention is to provide a method for quantitative determination of oxidant which method is capable of accurately and rapidly performing quantitative determination of oxidant at low cost, and an apparatus for quantitative determination of oxidant used in the method.

Solutions to the Problems

During a process to eagerly study a method for quantitative determination of oxidant, the inventors have found the following fact to complete the present invention. That is, one kind of reducing agent is added to a sample solution containing one or a plurality of kinds of oxidants having different lifetimes, an absorbance curve is produced by measuring a time change in absorbance of the post-color-change or post-coloring reducing agent, and the use of the absorbance curve can perform the quantitative determination of oxidant without being affected by the blank coloring caused by the natural oxidation of the reducing agent. That is, the method for quantitative determination of oxidant according to the present invention is a method for quantitative determination of oxidant performing quantitative determination of oxidant in a sample using a redox reaction, the method including: adding one kind of reducing agent to a sample solution containing one or a plurality of kinds of oxidants having different lifetimes; producing an absorbance curve by measuring a time change in absorbance of the post-color-change or post-coloring reducing agent; and performing the quantitative determination of the oxidant while identifying the oxidant in the sample solution based on the obtained absorbance curve.

The apparatus for quantitative determination of oxidant according to the present invention is an apparatus for quantitative determination of oxidant used in a method for quantitative determination of oxidant performing quantitative determination of oxidant in a sample using a redox reaction, the apparatus including a measuring unit and a controller, wherein the measuring unit includes: a reaction unit that causes a sample solution containing one or a plurality of kinds of oxidants having different lifetimes to react with one kind reducing agent; a light source that irradiates the reaction unit with light; and a light receiver that detects light transmitted through the reaction unit to measure an absorbance of the post-color-change or post-coloring reducing agent, and the controller includes: a storage in which a standard approximate curve indicating a time change in absorbance of a well-known oxidant and a calibration curve indicating a relationship between the absorbance and a concentration for the well-known oxidant are stored; and a calculator that produces an absorbance curve by measuring a time change in absorbance of the post-color-change or post-coloring reducing agent, and performs the quantitative determination of the oxidant while identifying the oxidant in the sample solution based on the obtained absorbance curve.

In the method for quantitative determination of oxidant according to the present invention, one kind of reducing agent can be used with respect to various oxidants, and the necessity of masking agent or blank test is eliminated. Therefore, the quantitative determination of oxidant can be accurately and rapidly performed at low cost.

MODE FOR CARRYING OUT THE INVENTION

Hereinafter, an exemplary embodiment of the present invention will be described with reference to the drawings.

A target oxidant in the present invention is not particularly limited. Preferably, the oxidant is an oxidant that can oxidize iodide ions. Examples of such an oxidant include hydrogen peroxide, ozone, radical species, potassium nitrate, hypochlorous acid, chlorous acid, chloric acid, perchloric acid, halogen, permanganate, ceric ammonium nitrate, chromic acid, dichromic acid, and peroxide. However, in the case where at least two kinds of oxidants exist, it is necessary that a lifetime difference exist in the oxidants. When the lifetime difference exists, the quantitative determination can be performed to all oxidants from stable oxidants (such as hydrogen peroxide) having long lifetime to unstable oxidants (such as ozone and radical species) having short lifetime irrespective of the kinds of the oxidants.

There is no particular limitation to a reducing agent as long as the reducing agent is soluble in water and exerts a color change or coloring during reaction with the oxidant, the color change or coloring being able to be detected by an optical method. Examples of the reducing agent include potassium iodide and ferrous sulfate, and potassium iodide is preferably used. In the present invention, the necessity of masking agent or masking treatment is eliminated. The masking agent means an agent that prevents the reducing agent from reacting with an oxidant except the target oxidant. The term "masking treatment" includes not only the addition of the masking agent but also a chemical modification of the reducing agent for the purpose of the prevention of the reducing agent from reacting with an oxidant except the target oxidant.

Figure 1:
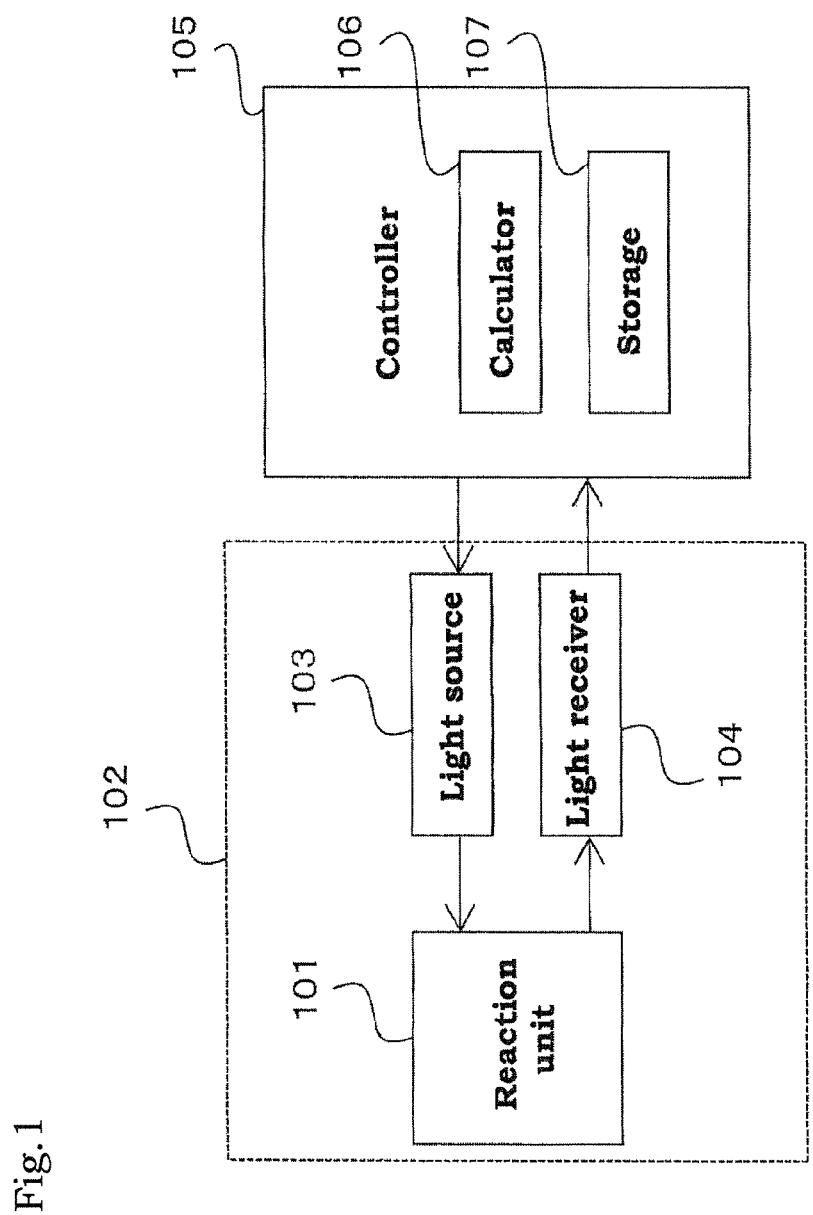
FIG. 1 is a schematic diagram illustrating a configuration example of an apparatus for quantitative determination according to the present invention.

FIG. 1 is a schematic diagram illustrating a configuration example of the apparatus for quantitative determination according to the present invention. The apparatus includes at least a measuring unit 102 and a controller 105. The measuring unit 102 includes a reaction unit 101 that causes a sample solution containing one or a plurality of kinds of oxidants having different lifetimes to react with one kind of reducing agent, a light source 103 that irradiates the reaction unit 101 with light, and a light receiver 104 that detects light transmitted through the reaction unit 101 to measure an absorbance of the post-color-change or post-coloring reducing agent. The controller 105 includes a storage 107 and a calculator 106. The storage 107 stores a standard approximate curve indicating a time change in absorbance of the well-known oxidant and a calibration curve indicating a relationship between the absorbance and a concentration. The calculator 106 measures the time change in absorbance of the post-color-change or post-coloring reducing agent to produce an absorbance curve, breaks down the obtained absorbance curve into at least one kind of approximate curve by a curve approximate analysis to calculate a half-value width of each approximate curve and initial absorbance at the time of zero, compares the half-value width of each approximate curve to a half-value width of the standard approximate curve of the well-known oxidant to identify the oxidant attributing to each approximate curve, and also performs the quantitative determination of the identified oxidant using the initial absorbance and a separately-acquired calibration curve indicating a relationship between the absorbance and the concentration for the well-known oxidant. The storage 107 may be connected to the outside. The reaction unit 101 may be provided independently of the measuring unit 102. An absorbance curve that is separately obtained by measuring the time change in absorbance of the well-known oxidant to which one kind of reducing agent is added can be used as the standard approximate curve of the well-known oxidant.

A procedure of the method for quantitative determination of oxidant according to the present invention will be described below with reference to FIG. 1. In the reaction unit 101, one kind of reducing agent is added to a sample solution containing at least one kind of oxidant. An optical cell can be used as the reaction unit 101. A quartz cell, a glass cell, or a disposable cell made of polystyrene or polymethylmethacrylate can be used as the optical cell.

Then, the measuring unit 102 irradiates the reaction unit 101 with light emitted from the light source 103 through an optical system (not illustrated), and the light receiver 104 detects light transmitted through the reaction unit 101. An ultraviolet visible light spectrophotometer can be used as the measuring unit 102.

Data of the transmitted light is sent from the light receiver 104 to the calculator 106. The calculator 106 calculates the absorbance of the post-color-change or post-coloring reducing agent from a comparison to data of light incident from the light source 103, and produces the absorbance curve representing the time change in absorbance of the reducing agent. Then, the curve approximate analysis is applied to the obtained absorbance curve to break down the absorbance curve into at least one kind of approximate curve, and the half-value width of each approximate curve and the initial absorbance at the time of zero are calculated. Then, the oxidant attributing to each obtained approximate curve is identified by comparing the half-value width of each obtained approximate curve with the half-value width of the standard approximate curve of the well-known oxidant, the standard approximate curve being separately acquired and stored in the storage 107. The half-value width obtained from the approximate curve can be used as a parameter indicating ease of attenuation of each oxidant, and the half-value width exhibits a unique value of each oxidant. Therefore, an unknown oxidant can be identified by comparing the half-value width of the unknown oxidant in the sample with the half-value width of the well-known oxidant. The quantitative determination of the identified oxidant is performed using the initial absorbance and the calibration curve indicating the relationship between the absorbance and the concentration for the well-known oxidant, the calibration curve being separately acquired and stored in the storage 107.

The calibration curve of the well-known oxidant is stored in the storage 107. In the production of the calibration curve, the reducing agent is similarly added to the oxidant having a well-known concentration, and the initial absorbance is measured at the time of zero. The calibration curve is produced using the initial absorbance and the concentration. Then, the absorbance curve is produced with respect to at least one kind of concentration, the curve approximate analysis is applied to the obtained absorbance curve to break down the absorbance curve into one kind of approximate curve, and the half-value width of the approximate curve is calculated. This half-value width is stored as the half-value width of the well-known oxidant. For example, for hydrogen peroxide, the concentration measured by the potassium permanganate method can be used as the concentration for producing the calibration curve. For ozone, the concentration measured using an ozone measurement reagent (produced by Kasahara Chemical Instruments Corp.) can be used as the concentration for producing the calibration curve.

There is no particular limitation to the curve approximate analysis used in the present invention as long as the distribution waveforms of various pieces of time-series data is approximated using a mathematical formula. Examples of the curve approximate analysis include Gaussian approximation, Maxwell-Boltzmann approximation, and Lorentz approximation, and Gaussian approximation is preferably used.

In the present invention, one kind of reducing agent can be used with respect to various oxidants. The necessity of masking agent or blank test is eliminated. Therefore, the quantitative determination of oxidant can be accurately and rapidly performed at low cost.

The present invention is usefully applied to the case where sample water containing at least two kinds of oxidants having different lifetimes is used as a target. In the case where a plurality of kinds of oxidants exist, the accurate quantitative determination of each oxidant is hardly performed by a conventional technique. For example, an enzymatic method or an absorbance method using leuco dye, which is of a conventional method for quantitative determination of hydrogen peroxide, can exert a quantitative capability in the case where the oxidant in the solution is only hydrogen peroxide. However, in the case where another oxidant except hydrogen peroxide exists (particularly, in the case where the oxidant, such as ozone or OH radicals, in which an oxidation potential is higher than that of hydrogen peroxide, exists), the accurate quantitative determination is hardly performed because the reducing agent also reacts with another oxidant. For a potassium iodide method that is of a conventional method for quantitative determination of ozone, the quantitative capability can be exerted in the case where the oxidant in the solution is only ozone. However, in the case where another oxidant except ozone exists, an ozone concentration is estimated to be higher because the potassium iodide also reacts with another oxidant, which hardly performs the accurate quantitative determination. The present invention focuses on the fact that the plurality of kinds of oxidants have different lifetimes in the case where the plurality of kinds of oxidants exist, and the half-value widths of the plurality of approximate curves obtained by applying the curve approximate analysis to the absorbance curve representing the time change in absorbance of the sample water exhibit the unique values of the oxidants. Accordingly, an unknown oxidant in the sample water can easily be identified by comparing the half-value width of each oxidant in the sample water with the half-value width of the well-known oxidant. The absorbance at the time of zero of the approximate curve obtained with respect to each oxidant in the sample water is proportional to the concentration of each oxidant, so that the concentration of each oxidant can be separately calculated using the calibration curve.

Additionally, the present invention is usefully applied to sample water containing radical species. For example, in particular, the present invention is usefully applied to the case where a plurality of kinds of oxidants such as ozone, hydrogen peroxide, and an oxygen-containing radical are generated in a solution by an in-liquid plasma device. When the plurality of kinds of oxidants such as ozone, hydrogen peroxide, and radicals are generated in a solution by an in-liquid plasma device, the quantitative determination of a product is hardly performed because the reaction of the oxidants with each other and the time change are competitively intertwined in the reaction mechanism of the solution (for example, OH radicals have short lifetime, and the radicals recombine with each other to form hydrogen peroxide). As described above, because the present invention focuses on the fact that the plurality of kinds of oxidants have different lifetimes in the case where the plurality of kinds of oxidants exist, a difference of the half-value width is increased with increasing lifetime difference, and the identification is easy to be performed. The concentrations of radical species and those of other oxidants except the radical species can be separately calculated using the absorbance at the time of zero of the approximate curve obtained with respect to each oxidant in the sample water.

EXAMPLES

Example 1

In Example 1, sample water containing hydrogen peroxide as an oxidant was used as a measurement target.
(Experimental Method)

The sample water was prepared by adding a predetermined amount of hydrogen peroxide (produced by KANTO CHEMICAL CO., INC.) to 250 mL of pure water. The time immediately after the addition was set to 0 minutes, 10 mL of pure water and a reducing agent mainly containing potassium iodide were added to the reaction unit 101 configured of a disposable cell (made of polymethylmethacrylate) having a cell length of 1 cm after predetermined time elapsed. The absorbance of the sample water (hereinafter, referred to as reduction treatment water) to which the reducing agent was added was measured at each predetermined time with the measuring unit 102. Using an ultraviolet visible light spectrophotometer (manufactured by JASCO Corporation), the absorbance was measured in a wavelength range of 400 nm to 800 nm, at measurement intervals of 1.0 nm, at a band width of 2.0 nm, and with a scanning speed of 400 nm/minute.

Using the absorbance data at each predetermined time, the controller 105 produced a graph (absorbance curve) indicating a relationship between the absorbance of a maximum peak of iodine in the wavelength range of 500 nm to 530 nm and the elapsed time.

(Production of Calibration Curve)

Five kinds of hydrogen peroxide water in which the concentration range was adjusted to $1.3 \times 10^{-5}$ to $6.3 \times 10^{-4}$ mol/L were used to produce the calibration curve of hydrogen peroxide. The concentration of hydrogen peroxide used to produce the calibration curve was measured by the potassium permanganate method. The acquired calibration curve data was stored in the storage 107.

Then, the calibration curve was produced by the following procedure. That is, with respect to hydrogen peroxide water having each concentration, pure water and a reducing agent mainly containing potassium iodide were added to the reaction unit 101 configured of a disposable cell (made of polymethylmethacrylate) having a cell length of 1 cm. The initial absorbance was measured at the time of zero, and the calibration curve was produced using the initial absorbance and the concentration. The absorbance of the reduction treatment water was measured at each predetermined time with the measuring unit 102 with respect to one kind of concentration. Then, a graph (absorbance curve) indicating a relationship between the absorbance of a maximum peak of iodine in the wavelength range of 500 nm to 530 nm and the elapsed time was produced using the absorbance data at each predetermined time. The Gaussian approximation was applied to the obtained absorbance curve to determine a Gaussian curve (called a standard Gaussian curve), and the data of the standard Gaussian curve was stored in the storage 107. The absorbance measurement was performed similarly as above.

(Result)

Figure 2:
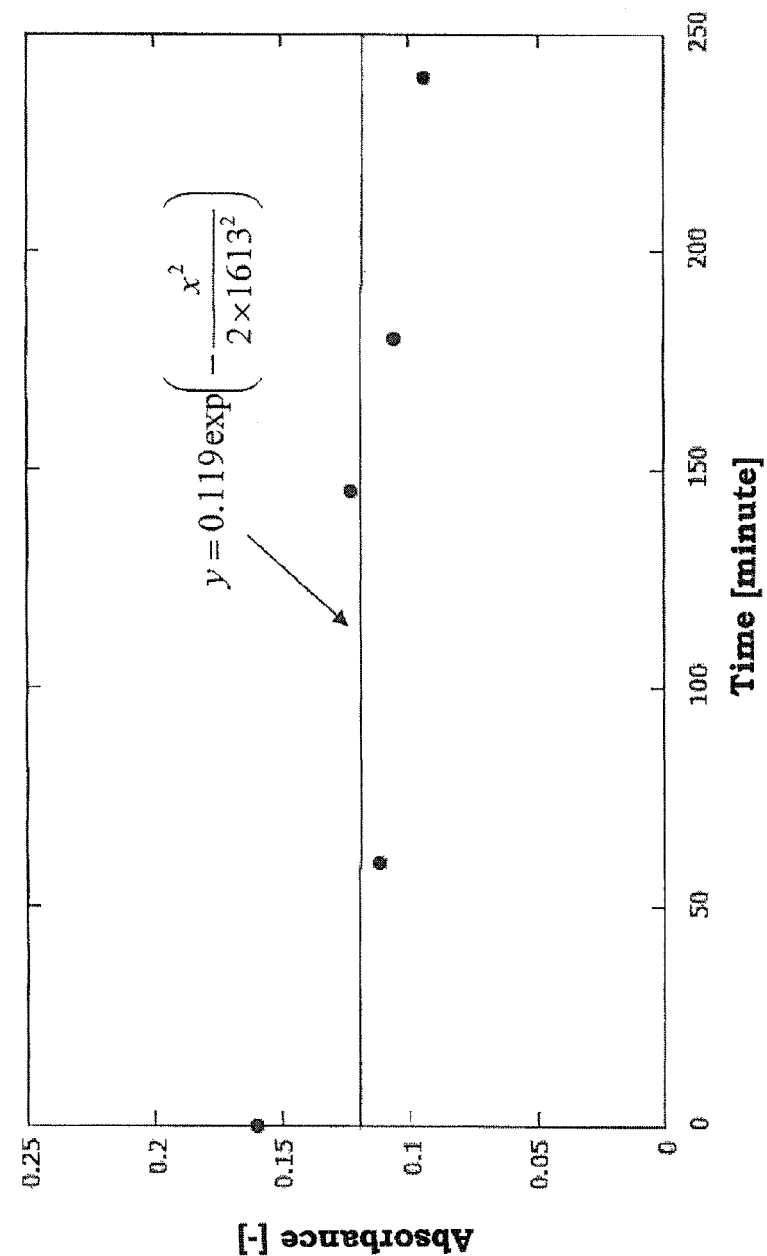
FIG. 2 is a graph illustrating a time change in absorbance of a sample in Example 1 of the present invention.

FIG. 2 is a graph illustrating the relationship between the absorbance of the maximum peak in the wavelength range of 500 nm to 530 nm and the elapsed time. In FIG. 2, the black circle (•) indicates a value of the absorbance of the maximum peak in the wavelength range of 500 nm to 530 nm. The calculator 106 determined the Gaussian curve by applying the Gaussian approximation with respect to the absorbance curve in FIG. 2. The obtained Gaussian curve (also called a Gaussian function) is illustrated as follows.

$$y = 0.119 \exp\left(-\frac{x^2}{2 \times 1613^2}\right)$$ [Mathematical formula 1]

Figure 3:
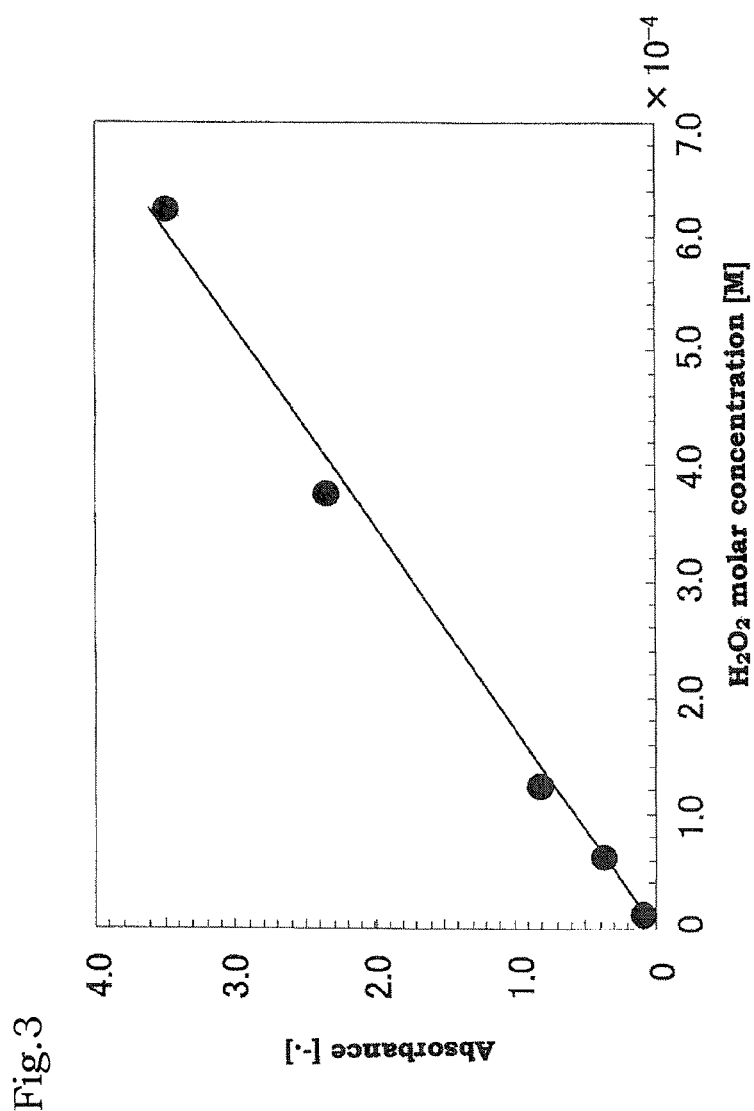
FIG. 3 is a graph illustrating an example of a calibration curve of hydrogen peroxide in Example 1 of the present invention.

FIG. 3 illustrates the calibration curve of hydrogen peroxide. The absorbance at the time of zero in the Gaussian curve corresponds to the hydrogen peroxide concentration at the time when the sample water was prepared, so that the hydrogen peroxide concentration in the sample water can be calculated using the absorbance at the time of zero. The absorbance at the time of zero was determined from the Gaussian curve, and the hydrogen peroxide concentration was calculated using the calibration curve of hydrogen peroxide in FIG. 3, the calibration curve being stored in the storage 107. A value of $2.5 \times 10^{-4}$ mol/L was obtained as the hydrogen peroxide concentration in the sample water. The half-value width of the Gaussian curve obtained with respect to the sample water was coincident well with the half-value width obtained from the standard Gaussian curve of hydrogen peroxide.

Example 2

In Example 2, sample water containing ozone as an oxidant was used as a measurement target.

(Experimental Method)

An air pump was connected to an ozone generator (manufactured by Chuen Electronics Co., Ltd), and the generated ozone was introduced to pure water, thereby preparing the sample water. The initial absorbance was measured at the time of zero, and the calibration curve was produced using the initial absorbance and the concentration. The time immediately after the addition was set to 0 minutes, 10 mL of pure water and a reducing agent mainly containing potassium iodide were added to the reaction unit 101 configured of a disposable cell (made of polymethylmethacrylate) having a cell length of 1 cm after predetermined time elapsed. The absorbance of the reduction treatment water was measured at each predetermined time with the measuring unit 102. The absorbance measurement was performed in the same manner as in Example 1.

Using the absorbance data at each predetermined time, the controller 105 produced a graph (absorbance curve) indicating a relationship between the absorbance of a maximum peak of iodine in the wavelength range of 500 nm to 530 nm and the elapsed time.

(Production of Calibration Curve)

Five kinds of aqueous ozone solution in which the concentration range was adjusted to $1.0 \times 10^{-5}$ to $3.1 \times 10^{-5}$ mol/L were used to produce the calibration curve of ozone. The acquired calibration curve data was stored in the storage 107. The ozone concentration used to produce the calibration curve was measured using an ozone measurement reagent (produced by Kasahara Chemical Instruments Corp.).

Then, the calibration curve was produced by the following procedure. With respect to the ozone water having each concentration, pure water and a reducing agent mainly containing potassium iodide were added to the reaction unit 101 configured of a disposable cell (made of polymethylmethacrylate) having a cell length of 1 cm. The initial absorbance was measured at the time of zero, and the calibration curve was produced using the initial absorbance and the concentration. The absorbance of the reduction treatment water was measured at each predetermined time with the measuring unit 102 with respect to one kind of concentration. Then, a graph (absorbance curve) indicating a relationship between the absorbance of a maximum peak of iodine in the wavelength range of 500 nm to 530 nm and the elapsed time was produced using the absorbance data at each predetermined time. The Gaussian approximation was applied to the obtained absorbance curve to determine a Gaussian curve (called a standard Gaussian curve), and the data of the standard Gaussian curve was stored in the storage 107.

(Result)

Figure 4:
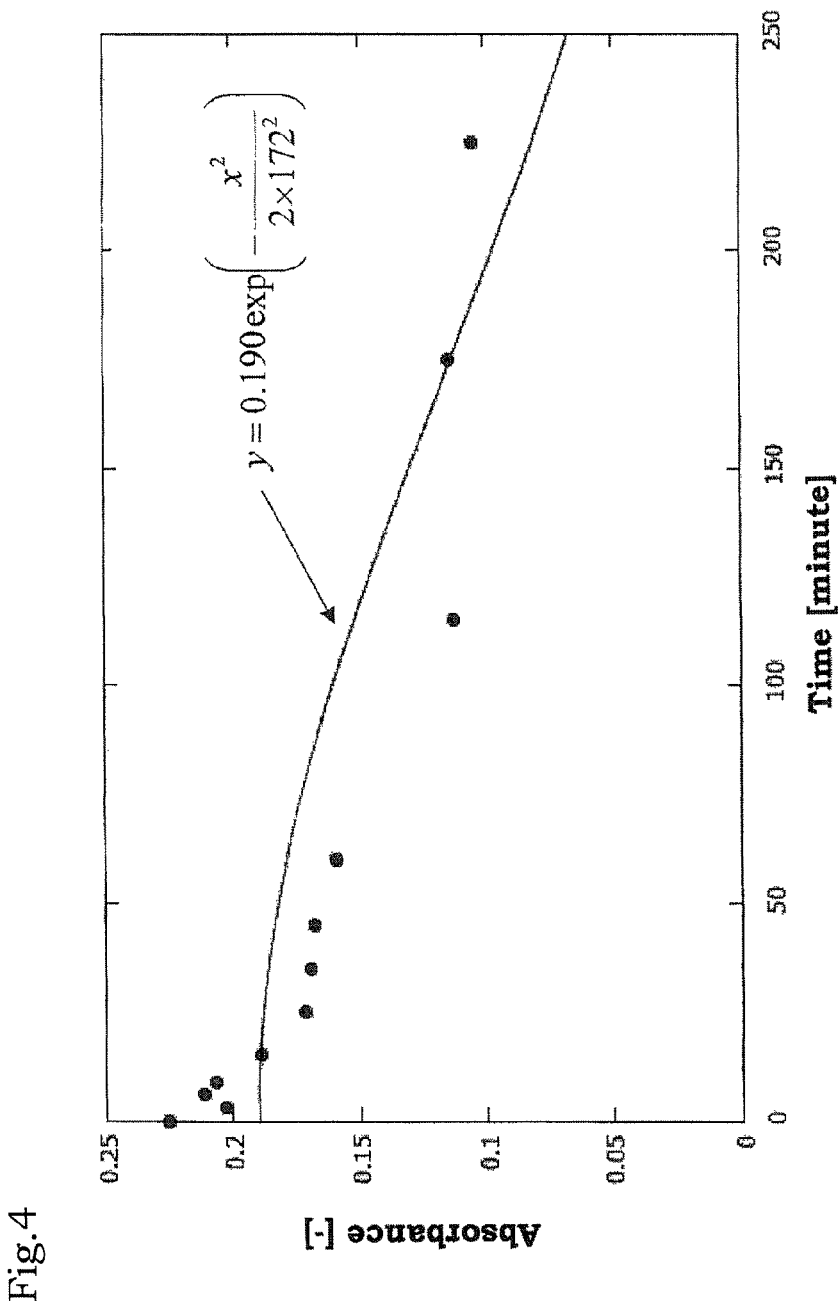
FIG. 4 is a graph illustrating the time change in absorbance of a sample in Example 2 of the present invention.

FIG. 4 is a graph illustrating the relationship between the absorbance of the maximum peak in the wavelength range of 500 nm to 530 nm and the elapsed time. In FIG. 4, the black circle (•) indicates a value of the absorbance of the maximum peak in the wavelength range of 500 nm to 530 nm. The calculator 106 determined the Gaussian curve by applying the Gaussian approximation with respect to the absorbance curve in FIG. 4. The obtained Gaussian curve is illustrated as follows.

$$y = 0.190 \exp\left(-\frac{x^2}{2 \times 172^2}\right)$$ [Mathematical formula 2]

Figure 5:
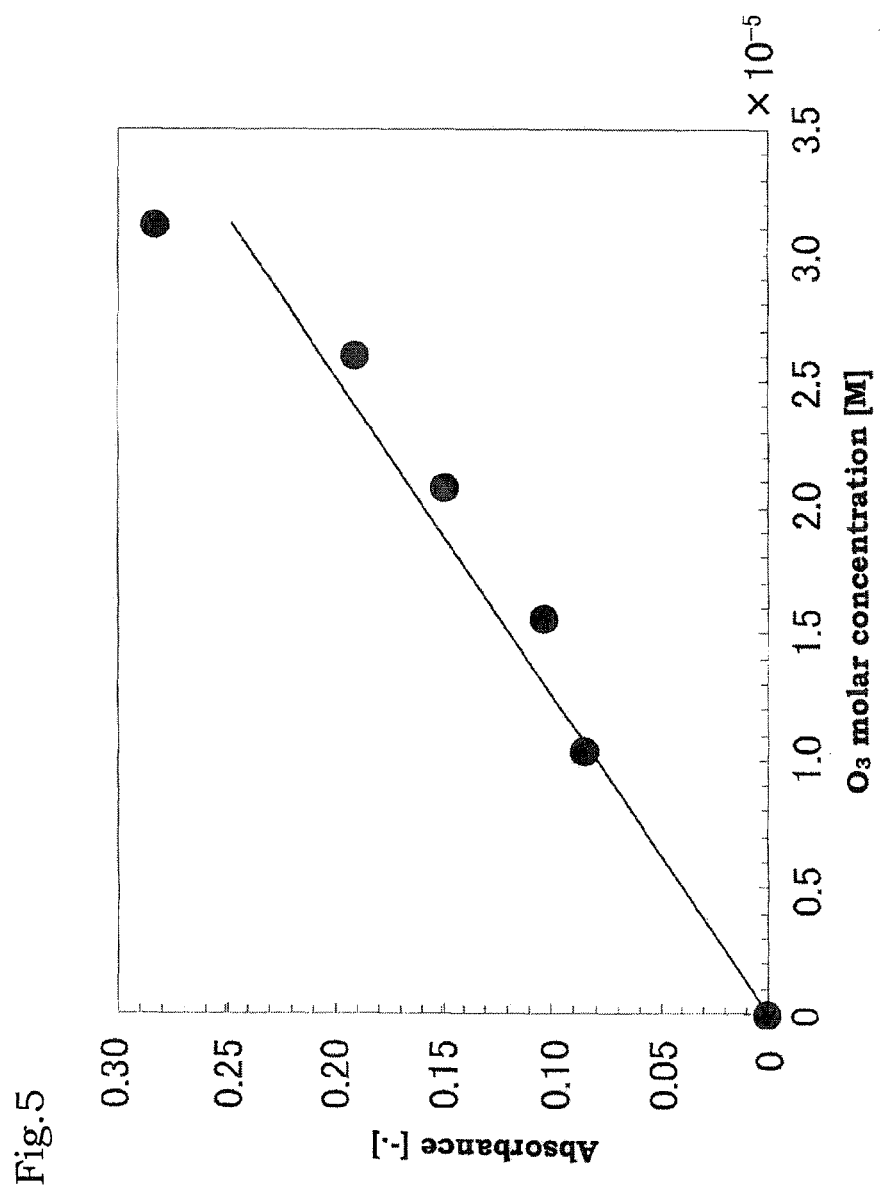
FIG. 5 is a graph illustrating an example of the calibration curve of ozone in Example 2 of the present invention.

FIG. 5 illustrates the calibration curve of ozone. The absorbance at the time of zero was determined from the Gaussian curve, and the ozone concentration was calculated using the calibration curve of ozone in FIG. 5, the calibration curve being stored in the storage 107. A value of $1.3 \times 10^{-6}$ mol/L was obtained as the ozone concentration in the sample water. The half-value width of the Gaussian curve obtained with respect to the sample water was coincident well with the half-value width obtained from the standard Gaussian curve of ozone.

Example 3

In Example 3, sample water containing ozone and hydrogen peroxide as oxidants was used as a measurement target.
(Experimental Method)

The sample water was prepared by adding predetermined amounts of ozone and hydrogen peroxide (produced by KANTO CHEMICAL CO., INC.) to 250 mL of pure water. An air pump was connected to an ozone generator (manufactured by Chuen Electronics Co., Ltd) to dissolve ozone into the pure water. The time immediately after the addition was set to 0 minutes, 10 mL of pure water and a reducing agent mainly containing potassium iodide were added to the reaction unit 101 configured of a disposable cell (made of polymethylmethacrylate) having a cell length of 1 cm after predetermined time elapsed. The absorbance of the sample water (hereinafter, referred to as reduction treatment water) to which the reducing agent was added was measured at each predetermined time with the measuring unit 102. The absorbance measurement was performed in the same manner as in Example 1.

The absorbance data was sent to the controller 105 at each predetermined time, and the controller 105 produced a graph (absorbance curve) indicating a relationship between the absorbance of a maximum peak of iodine in the wavelength range of 500 nm to 530 nm and the elapsed time.
(Result)

Figure 6:
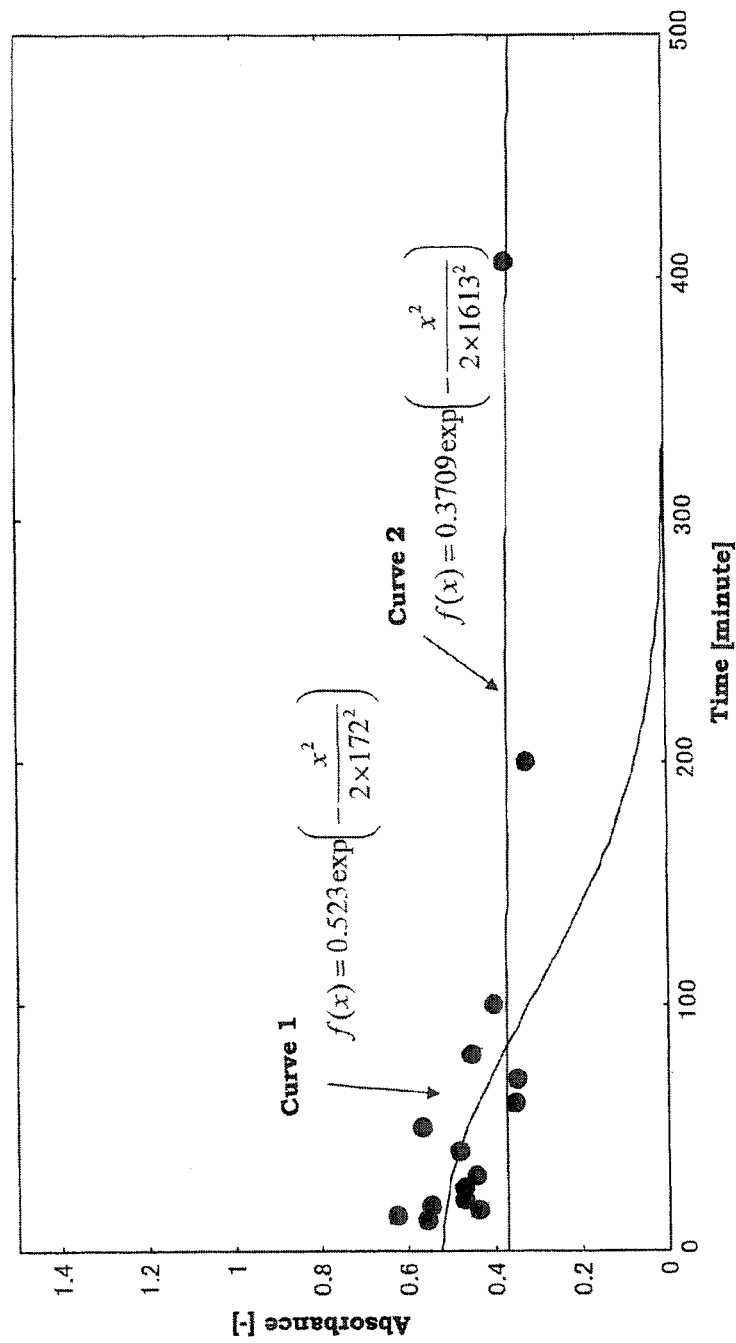
FIG. 6 is a graph illustrating the time change in absorbance of a sample in Example 3 of the present invention.

FIG. 6 is a graph illustrating the relationship between the absorbance of the maximum peak in the wavelength range of 500 nm to 530 nm and the elapsed time. In FIG. 6, the black circle (•) indicates a value of the absorbance of the maximum peak in the wavelength range of 500 nm to 530 nm. As can be seen from FIG. 6, there are an attenuation area (hereinafter, referred to as an A area) of about 20 minutes to about 100 minutes and a stable attenuation area (hereinafter, referred to as a B area) where the concentration is kept constant after about 100 minutes.

The calculator 106 determined the Gaussian curve by applying the Gaussian approximation with respect to the A area and B area of the absorbance curve in FIG. 6. The obtained Gaussian curve is illustrated as follows.

Curve 1 (A area)

$$y = 0.523 \exp\left(-\frac{x^2}{2 \times 172^2}\right)$$ [Mathematical formula 3]

Curve 2 (B area)

$$y = 0.371 \exp\left(-\frac{x^2}{2 \times 1613^2}\right)$$ [Mathematical formula 4]

The half-value width of the Gaussian curve is a parameter representing the lifetime of each oxidant, the curve 1 has a half-value width of $2 \times 172^2$, and the curve 2 has a half-value width of $2 \times 1613^2$. The half-value widths were compared with the half-value widths of the standard Gaussian curves of ozone and hydrogen peroxide, the standard Gaussian curves being produced in Examples 1 and 2 and stored in the storage 107, and it was confirmed that the half-value widths of the standard Gaussian curves are coincident with the half-value widths of the curves 1 and 2.

The absorbance at the time of zero was determined from each of the curves 1 and 2 in FIG. 6, and the ozone and hydrogen peroxide concentrations were calculated using the calibration curves of ozone and hydrogen peroxide, the calibration curves being stored in the storage 107. In Example 3, in the sample water, the ozone concentration was $2.5 \times 10^{-5}$ mol/L, and the hydrogen peroxide concentration was $6.9 \times 10^{-5}$ mol/L.

Example 4

In Example 4, sample water containing radical species, ozone and hydrogen peroxide as oxidants was used as a measurement target.

As to a procedure to prepare the sample, 250 mL of pure water (having an electric conductivity of 20 mS/m, prepared by mixing sodium sulfate) was subjected to plasma treatment for 10 minutes. The time immediately after the plasma treatment was set to 0 minutes, and 10 mL of the sample and a reducing agent mainly containing potassium iodide were added to the reaction unit 101 after a constant time elapsed. The absorbance of the reduction treatment water was measured at each predetermined time with the measuring unit 102. The absorbance measurement was performed in the same manner as in Example 1.
(Result)

Figure 7:
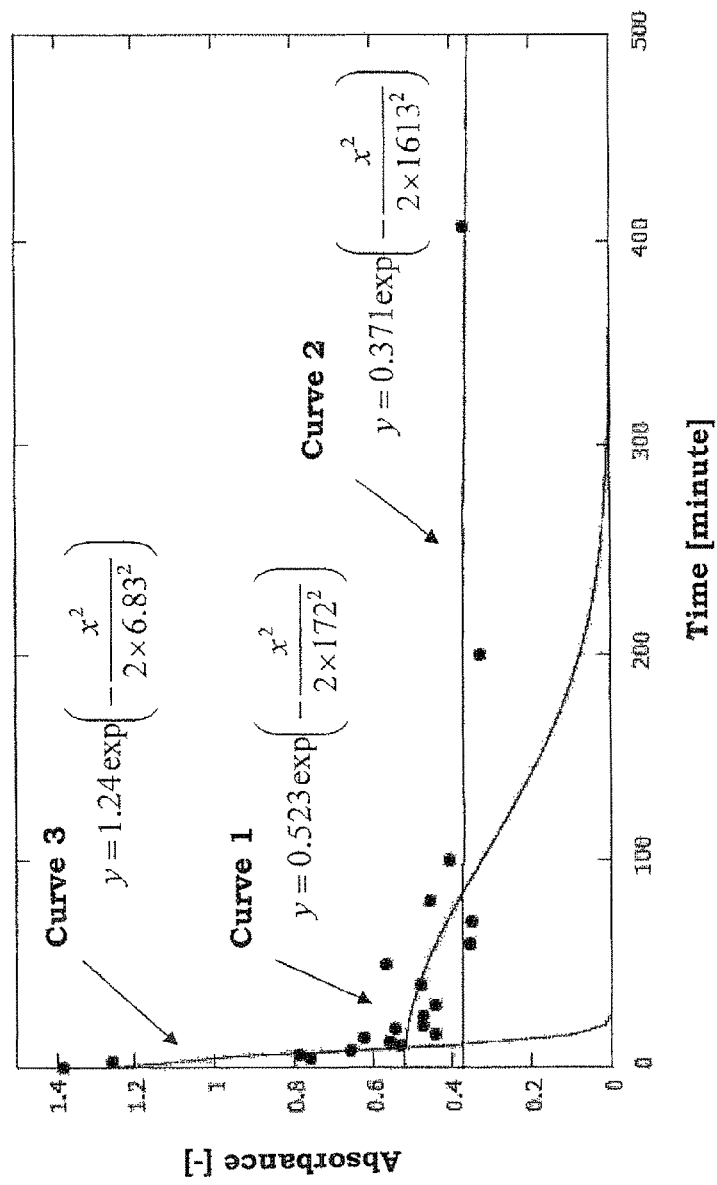
FIG. 7 is a graph illustrating the time change in absorbance of a sample in Example 4 of the present invention.

FIG. 7 is a graph illustrating a relationship between the absorbance of a maximum peak in the wavelength range of 500 nm to 530 nm and the elapsed time. In FIG. 7, the black circle (•) indicates a value of the absorbance of the maximum peak in the wavelength range of 500 nm to 530 nm. As can be seen from FIG. 7, there are an attenuation area (hereinafter, referred to as a C area) of 0 to about 20 minutes, the attenuation area (referred to as the A area) of about 20 minutes to about 100 minutes, and the stable attenuation area (B area) where the concentration is kept constant after about 100 minutes.

The calculator 106 determined the Gaussian curve by applying the Gaussian approximation with respect to the A area, B area, and C area of the absorbance curve in FIG. 7. The obtained Gaussian curve (also called a Gaussian function) is illustrated as follows.

Curve 1 (A area)

$$y = 0.523 \exp\left(-\frac{x^2}{2 \times 172^2}\right)$$ [Mathematical formula 5]

-continued

Curve 2 (B area)

$$y = 0.371 \exp\left(-\frac{x^2}{2 \times 1613^2}\right) \quad \text{[Mathematical formula 6]}$$

Curve 3 (C area)

$$y = 1.24 \exp\left(-\frac{x^2}{2 \times 6.83^2}\right) \quad \text{[Mathematical formula 7]}$$

The curve 1 has a half-value width of $2 \times 172^2$, and the curve 2 has a half-value width of $2 \times 1613^2$. The half-value widths were compared with the half-value widths of the standard Gaussian curves of ozone and hydrogen peroxide, the standard Gaussian curves being produced in Examples 1 and 2 and stored in the storage 107, and it was confirmed that the half-value widths of the standard Gaussian curves are coincident with the half-value widths of the curves 1 and 2. The curve 3 can be estimated to attribute to radical species because the oxidant of the curve 3 is different from that of hydrogen peroxide or ozone, for example, because the attenuation time is short.

The absorbance at the time of zero was obtained from each of the curves 1 and 2 in FIG. 7, and the ozone and hydrogen peroxide concentrations were calculated using the calibration curves of ozone and hydrogen peroxide, the calibration curves being stored in the storage 107. In Example 4, in the sample water, the ozone concentration was $2.5 \times 10^{-5}$ mol/L, and the hydrogen peroxide concentration was $6.9 \times 10^{-5}$ mol/L.

INDUSTRIAL APPLICABILITY

According to the present invention, using one kind of reducing agent, the quantitative determination of oxidant can be accurately and rapidly performed at low cost without being affected by blank coloring caused by the natural oxidation of the reducing agent. Particularly, even if a plurality of kinds of oxidants coexist in sample water, the accurate quantitative determination of concentration of each oxidant can be performed. Therefore, the present invention is usefully applied to monitoring of water quality and operation management of a water treatment apparatus. The present invention is also applied to the quantitative determination of various components existing in a body fluid in a clinical inspection or an environmental analysis.

DESCRIPTION OF SYMBOLS

101 Reaction unit
102 Measuring unit
103 Light source
104 Light receiver
105 Controller
106 Calculator
107 Storage

What is claimed is:

1. A method for quantitative determination of an oxidant in a sample using a redox reaction, the method comprising:
adding one kind of reducing agent to a sample solution containing one or a plurality of kinds of oxidants having different lifetimes;
producing an absorbance curve by measuring a time change in absorbance of the sample solution after the one kind of reducing agent is added to the sample solution; and
performing the quantitative determination of the oxidant while identifying the oxidant in the sample solution based on the obtained absorbance curve, wherein
the oxidant in the sample solution is identified by comparing the obtained absorbance curve with a separately-acquired standard approximate curve indicating a time change in absorbance of a known oxidant,
the obtained absorbance curve is broken down into at least one kind of approximate curve by a curve approximate analysis to calculate a half-value width of each approximate curve and initial absorbance at a time of zero of each approximate curve, and
the half-value width of each approximate curve is compared with a half-value width of a separately-acquired standard approximate curve of the known oxidant to identify an oxidant attributing to each approximate curve.

2. The method for quantitative determination of oxidant according to claim 1, wherein the quantitative determination of the identified oxidant is performed using the initial absorbance and a separately-acquired calibration curve indicating a relationship between absorbance and a concentration for the known oxidant.

3. The method for quantitative determination of oxidant according to claim 1, wherein the approximate curve is a Gaussian curve.

4. An apparatus for quantitative determination of an oxidant in a sample using a redox reaction, the apparatus comprising
a measuring unit including:
a reaction unit that causes a sample solution containing one or a plurality of kinds of oxidants having different lifetimes to react with one kind reducing agent;
a light source that irradiates the reaction unit with light; and
a light receiver that detects light transmitted through the reaction unit to measure absorbance of the sample solution, and
a controller including:
a storage in which a standard approximate curve indicating a time change in absorbance of a known oxidant and a calibration curve indicating a relationship between absorbance and a concentration for the known oxidant are stored; and
a calculator that produces an absorbance curve by measuring a time change in absorbance of the sample solution after the one kind of reducing agent is added to the sample solution, and performs the quantitative determination of the oxidant while identifying the oxidant in the sample solution based on the absorbance curve, wherein
the calculator breaks down the absorbance curve into at least one kind of approximate curve by a curve approximate analysis to calculate a half-value width of each approximate curve and an initial absorbance at a time of zero of each approximate curve, compares the half-value width of each approximate curve with a half-value width of the standard approximate curve of the known oxidant to identify the oxidant attributing to each approximate curve, and performs the quantitative determination of the identified oxidant using the initial absorbance and a separately-acquired calibration curve indicating a relationship between absorbance and a concentration for the known oxidant.

5. A method, comprising:
(i) adding a reducing agent to a sample solution including oxidants having different lifetimes;
(ii) after the adding (i), obtaining an absorbance curve by measuring a time change in absorbance of the sample solution;
(iii) obtaining approximate curves from the absorbance curve by a curve approximate analysis; and
(iv) identifying the oxidants by comparing each of the approximate curves with standard approximate curves, each of the standard approximate curves being obtained from an absorbance curve indicating a time change in absorbance caused by a redox reaction between a known oxidant and the reducing agent, the standard approximate curves being different from each other,
wherein in the obtaining (iii), each of the approximate curves is a Gaussian curve.

6. The method according to claim 5, wherein
in the identifying (iv), each of the standard approximate curves is a Gaussian curve.

7. A method, comprising:
(i) adding a reducing agent to a sample solution including oxidants having different lifetimes;
(ii) after the adding (i), obtaining an absorbance curve by measuring a time change in absorbance of the sample solution;
(iii) obtaining approximate curves from the absorbance curve by a curve approximate analysis; and
(iv) identifying the oxidants by comparing each of the approximate curves with standard approximate curves, each of the standard approximate curves being obtained from an absorbance curve indicating a time change in absorbance caused by a redox reaction between a known oxidant and the reducing agent, the standard approximate curves being different from each other,
wherein
the identifying (iv) comprises:
(iv-1) calculating a half-value width of each of the approximate curves; and
(iv-2) identifying the oxidants by comparing the half-value width of each of the approximate curves with half-value widths of the standard approximate curves.

8. The method according to claim 5, further comprising:
(v) determining a quantity of each of the oxidants by applying absorbance at a time of zero of corresponding one of the approximate curves to a calibration curve, the calibration curve indicating a relationship between absorbance and a concentration of the known oxidant corresponding to the each of the oxidants.

9. The method according to claim 5, wherein the method is performed without a masking agent.

10. The method according to claim 5, wherein the method is performed without a blank test.

* * * * *